United States Patent [19]
Fiedler

[11] Patent Number: 5,592,945
[45] Date of Patent: Jan. 14, 1997

[54] REAL-TIME EVENT CHARTING IN AN ELECTRONIC FLOWSHEET

[75] Inventor: Steven P. Fiedler, Leominster, Mass.

[73] Assignee: Hewlett-Packard Company, Palo Alto, Calif.

[21] Appl. No.: 608,347

[22] Filed: Feb. 28, 1996

[51] Int. Cl.⁶ ................................................ A61B 5/0402
[52] U.S. Cl. ..................................... 128/710; 364/413.03
[58] Field of Search ......................... 364/413.01, 413.02, 364/413.03, 413.06; 128/710

[56] References Cited

U.S. PATENT DOCUMENTS

| | | |
|---|---|---|
| 5,247,611 | 9/1993 | Norden-Paul et al. . |
| 5,301,319 | 4/1994 | Thurman et al. . |
| 5,337,405 | 8/1994 | Lindauer et al. . |
| 5,361,202 | 11/1994 | Doue . |
| 5,447,164 | 9/1995 | Shaya et al. . |

OTHER PUBLICATIONS

Hewlett–Packard Company Brochure entitled "HP CareVue 9000—Now You Can Put Information In Its Place" Copyright 1989 #5959–2497.

*Primary Examiner*—William E. Kamm
*Assistant Examiner*—Scott M. Getzow
*Attorney, Agent, or Firm*—Mark Z. Dudley

[57] ABSTRACT

To improve real time charting of patient information in medical information system for a health care facility, a computer display system, and a method for such a display system, includes a displayed representation of the data sheet of an identified patient in the health care facility. In such a medical information system patient data is stored in data files in a database, wherein each data file in the database is comprised of a plurality of data records. A user positions a cursor on the displayed representation of data sheet provided in the form of an electronic flowsheet, using an input unit, and signals the computer of a selected event. The computer, in response to the signal, determines the selected event from the position of the cursor, determines the current date and time, and accesses a data record or records from the data file based on the selected event and the current date and time. The accessed data record or records may then be modified by entry of a data value associated with the selected event at the current time. Data entry is expedited by the manipulation of the input unit to select the event and to enter a data value in the form of a data value entered by use of the input unit, or by acceptance of a default data value. Further manipulation of the input unit provides implicit acceptance of the entered data value or of a placeholder automatically provided in the absence of an entered data value. Operation of logic filtering is contemplated to enable implicit acceptance of the entered data value.

14 Claims, 6 Drawing Sheets

| | | TIME | r95 0AM | 10:00AM | 11:00AM | 22Mar95 12:00PM | | 02:00PM | 03:00PM |
|---|---|---|---|---|---|---|---|---|---|
| VITAL SIGNS | V i t a l s | HR ARTERIAL BP ANESTHESIA START INTUBATION | | | | | | | |
| INTAKE OUTPUT | | | | | | | | | |
| RESP | | EYE VENTILATOR SETTING | | | | | | | |
| LABS | D r i | DOPA(kg) mcg/kg/min LIDO mg/min BRENTLIUM mg/min | | | | | | | |
| MEDS | l & | DOPAMINE: mcg/kg/min LIDOCAINE BRETYLIUM | | | | | | | |
| TREAT MENTS | O | | | | | | | | |
| PHYSIO CALCS | M e | IV MEDS FLUIDS PO/NG MEDS FLUIDS | | | | | | | |
| GRAFIC VITALS | F | PEDAL PULSES – L | | | | | | | |

| | | | 95 0AM | 10:00AM | 11:00AM | 22Mar95 12:00PM | 02:00PM | 03:00PM |
|---|---|---|---|---|---|---|---|---|
| VITAL SIGNS | v i t a l s | HR | | | | | | |
| | | ARTERIAL BP | | | | | | |
| INTAKE OUTPUT | | ANESTHESIA START | | | | | | |
| | | INTUBATION | | | | | | |
| RESP | | EYE | | | | | | |
| | | VENTILATOR SETTING | | | | | | |
| LABS | D r i | DOPA(kg) mcg/kg/min | | | | | | |
| | | LIDO mg/min | | | | | | |
| | | BRENTLIUM mg/min | | | | | | |
| MEDS | | DOPAMINE: mcg/kg/min | | | | | | |
| | & | LIDOCAINE | | | | | NONE | |
| TREAT MENTS | O | BRETYLIUM | | | | | 6 | |
| PHYSIO CALCS | M e | IV MEDS FLUIDS | | | | | | |
| | | PO/NG MEDS FLUIDS | | | | | | |
| GRAFIC VITALS | F | PEDAL PULSES - L | | | | | | |

REAL-TIME EVENT CHARTING IN AN ELECTRONIC FLOWSHEET

FIELD OF THE INVENTION

This invention relates to information display systems which facilitate data entry of patient information stored in a database of a medical information system. More particularly, the invention is related to a medical information system which facilitates the task of charting a patient record, that is, the task of accessing, entry, and/or storage of patient data in a patient data record.

BACKGROUND OF THE INVENTION

Medical information systems are commonly used by health care facilities for storing patient information in electronic records that replace, for example, paper-based records. An example of such a medical information system is the HP CareVue 9000 system available from the Hewlett-Packard Company of Palo Alto, Calif.

While such systems provide highly satisfactory operation and have many advantages, a problem with conventional medical information systems is the difficulty with which a clinician may access and enter real-time patient data into a patient data record stored in the system. A portion of the patient data record is commonly called a "chart" and the task of accessing, entry, and/or storage of patient data associated with an care event or patient condition is considered to be "charting". Charting that is performed contemporaneously with the respective event will, for the purposes of this description, be considered "real-time charting."

A particular type of patient data record is known as a flowsheet. Flowsheets are records used by care givers to record vital signs, interventions, treatments, and activities pertaining to a patient for a given time interval. Flowsheets may exist in paper or electronic formats; both of the formats are often utilized in a health care facility. Flowsheets can contain various sections that organize patient data in either a tabular format (using a row and column arrangement) or in a graphical format. Most electronic flowsheets that are configured to allow a user to access or enter data stored in a data record are textually-based.

Data entry in a tabular electronic flowsheet is typically performed by locating and selecting a desired event type (typically organized as one of series of rows) and a time to be associated with the event type (typically organized as one of a series of columns). Data entry is performed by either a pointing device or keystrokes followed by entry of the appropriate values that represent the information to be recorded for that event. A sequence of pointing and clicking on a row label may, in some instances, provide access to more detailed information about the row (e.g., when the row was added to the flowsheet, the complete name and dose of a drug, etc.)

Data entry for certain events (e.g., events that occur in clinical environments) may be performed at periodic intervals and need not be recorded in real time. However, there is a need for data entry for certain events or conditions that are affected by the passage of time, such as surgical procedures in an operating room. The latter type of data should be charted in real time. However, due to the responsibilities of the care giver, real-time charting is difficult because the hands and mind of the care giver are usually occupied with other tasks.

The HP CareVue 9000 aids real-time entry of data by use of a charting dialog that is preconfigured to identify the current time. A charting dialog is provided, however, only if the user has already selected an appropriate column on the flowsheet; that is, the column that represents the current time. This procedure forces the user to first ensure that the correct column is displayed, then locate the intersection of the displayed column and the desired row, and then operate the system to obtain the charting dialog. These steps must be undertaken before real-time data entry can be performed.

Furthermore, there is a problem relating to the entry of temporary data which may subsequently be considered unnecessary and therefore be subject to editing or deletion. Users accustomed to a paper-based flowsheet traditionally have adopted a method of entry of temporary notations on an erasable or detachable medium. Paper flowsheets, when complete, are required to be recorded in ink. A user wishing to make such temporary notation will necessarily revise or recopy a paper flowsheet to remove or alter any unwanted notations. Such a practice not only creates clutter but also additional labor for the user. Systems that provide electronic flowsheets generally do not allow a user to leave any temporary notations on the flowsheet without also leaving an audit trail. Accordingly, with respect to the entry of temporary data on either a paper-based or electronic flowsheet, the conventional approaches are regarded as difficult or impractical.

SUMMARY OF THE INVENTION

One aspect of the present invention provides a method and apparatus for real-time charting of data to a patient data record in a data base stored in a medical information system.

Another aspect of the present invention provides a computer display system and method wherein a representation of a flowsheet is obtained from the patient data record and is displayed. This representation includes one or more data elements displayed in the flowsheet. The user positions a cursor on the display using an input unit for the computer and signals the computer of a desired data element. Preferably, the data element is associated with patient data such as a care event that references a patient care procedure or data indicative of the patient's condition. The computer, in response to a signal from the input unit, determines the current date and time and selects the desired data element. If the data element is not present for selection, the computer creates the data element. The computer then accesses the data element and associates the data element with the current date and time. The accessed data element is then modified to reflect the associated current date and time and any data entered by the user for the data element. The modified data element is stored in the data record. As a result, data records may be easily and rapidly accessed and updated to include data elements that are associated with the current date and time. Real time charting of the flowsheet is thereby enabled.

An embodiment of a computer display system constructed in accordance with the invention includes a database in which there is a file for each patient comprising a plurality of data records. The system also includes a processor which is coupled to a display and which controls display information of the display. A memory is coupled to the processor for storing display and other data. An input unit, which may include a keyboard or a cursor control device, is also coupled to the processor. The processor performs arithmetic and logic operations as may be directed by a computer program, accesses the memory to obtain display data representative of a data record in the database, and displays respective display data on the video display. In response to signals from the cursor control device, a cursor is positioned on the display. Manipulation of the input unit causes the cursor to be positioned on the event row to select the event row such that one or more data elements relevant to the respective event may be entered (if not already present) and associated with desired date and time. In a preferred embodiment, the desired date and time is defined as the current date and time. Further operation of the input unit provides signals indicative of a selection of the event row, the data element, and its association with the current date and time. In response to this determination of the current date and time, the processor accesses the data element in the data record. The accessed data record is modified to include a data value that may be a default data value or one entered by the user. The data value thus included is associated with the selected event at the current date and time. The modified data record is then displayed on the video display.

In one feature of the invention, the user may chart data values in an electronic flowsheet using but one hand to manipulate the input unit.

In another feature of the invention, the user may chart data values in an electronic flowsheet at the current time without resort to a search of the flowsheet for the column containing the current time.

In another feature of the invention, the user may enter a data value for an event when there is insufficient time for such data entry to signify insertion of a "placeholder" as a data element to reserve a position for later data entry. The placeholder may be subsequently edited to include a data value or cleared.

In another feature of the invention, the user may avoid reliance on his or her memory to reconstruct a sequence of events because the user is afforded the opportunity and capability to enter values and placeholders as needed, i.e., in real-time.

In another feature of the invention, the placeholders are temporary and cannot appear on a completed patient data record, so that the task of revision or recopying of the record (to remove unwanted notations) is obviated.

In another feature of the invention, the preferred method of data entry should increase productivity by allowing a user to perform data entry in a more efficient manner. The user may locate and select a desired row and signify the selection by manipulation of the input unit to initiate data entry. The additional time and effort of locating the column corresponding to the current time are thereby eliminated. In a preferred embodiment, the input unit is a switch-operated pointing device such as a mouse or trackball, and the user is able to chart an event contemporaneously with the event because only two "clicks" are required to accept a default value or to leave a placeholder on the flowsheet.

In another feature of the invention, the preferred method and apparatus utilize the pointing device for data entry so that the user is not forced to search for cursor manipulation or data entry keys on a traditional keyboard.

BRIEF DESCRIPTION OF THE DRAWINGS

FIGS. 3–5 are graphical illustrations of a series of displays for a display system in accordance with the present invention.

DETAILED DESCRIPTION OF THE INVENTION

Figure 1:
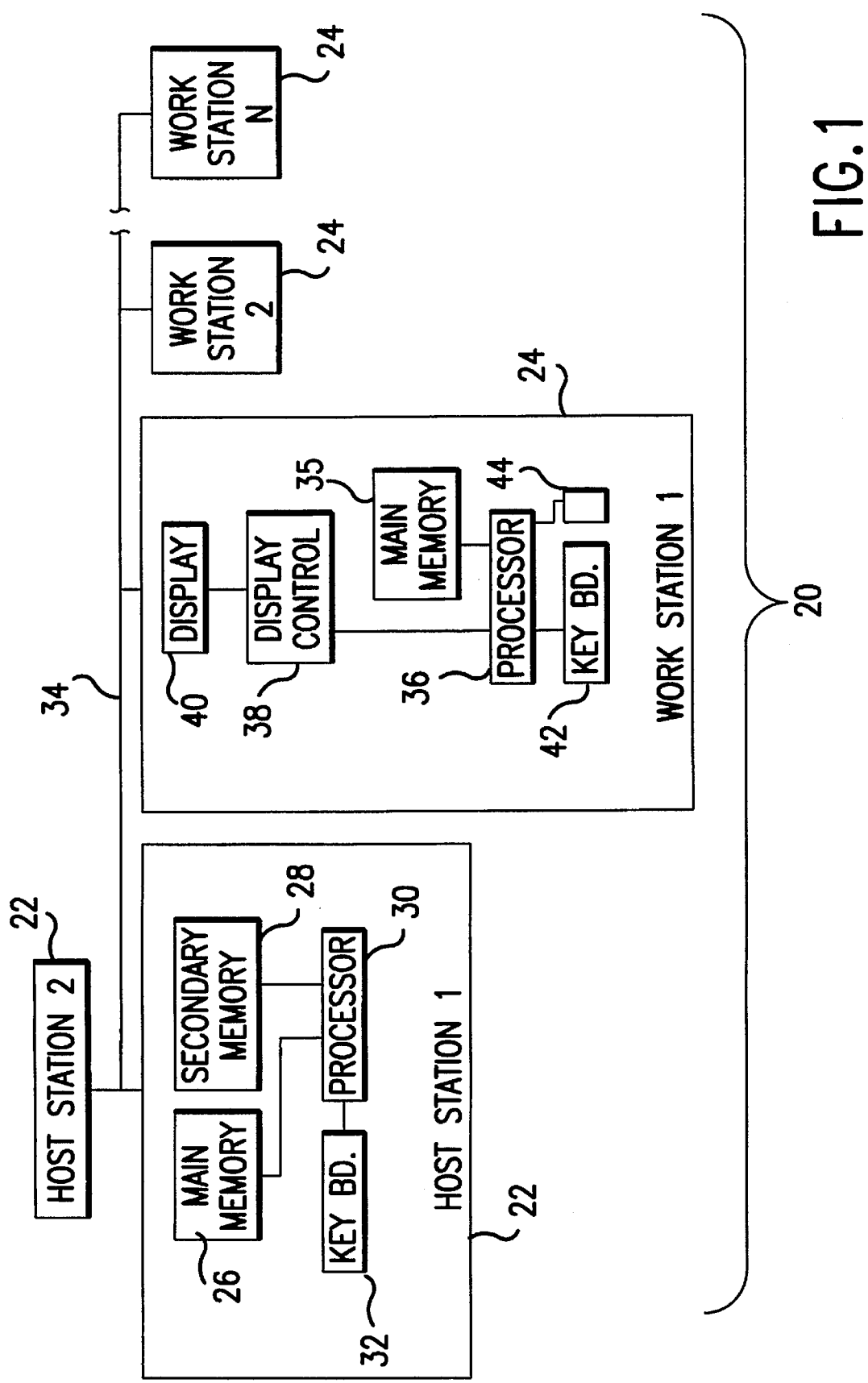
FIG. 1 is a block diagram of a data processing system suitable for an embodiment of the present invention.

The computer display system and method of the present invention are preferred for use in a medical information system which includes a database of patient information as in a health care information system. A data processing system 20, suitable for implementing a display system for a medical information system in accordance with the present invention, is illustrated in FIG. 1. The data processing system 20 includes at least one host station 22 and one or more workstations 24. A host station 22 includes a main memory 26 for holding data which may be used by users of the system. A secondary memory 28 is also provided for maintaining the integrity of the database. A processor 30 is provided for reading and writing of data from the database stored in memory 26, and for executing other operations requested by users at other host stations 22, at workstation 24 and/or at the input unit, such as a keyboard 32, for the host station. It is preferable to have a second host station 22 to provide a redundant database in case of failure of the first host station. The host stations are normally and preferably located at a central location within a hospital or other health care facility.

Workstations 24, on the other hand, are normally located within a particular care unit in a health care facility and are connected to the host stations 22 via a network 34. Workstation 24 normally includes a main memory 35 for storing local copies of data and programs and a processor 36 which is capable of performing read and write requests for data from its main memory, and performing other operations as directed by a computer program, such as logical and arithmetic operations, on data. The processor 36 also controls a display control 38 for controlling a display of information on a display 40. The workstation 24 also includes an input unit, such as a keyboard 42 or a cursor control device 44. A preferred embodiment of the input unit includes a keyboard 42 and a cursor control device 44 in the form of a pointing device such as mouse or a trackball. Preferably, a trackball or mouse with a plurality of switches is used as the cursor control device 44. Plural workstations 24, interconnected by network 34, are provided in a care unit. Preferably, a workstation 24 is provided for each patient room in the health care facility.

In the preferred embodiment at the time of filing this application, each workstation 24 was implemented as a Hewlett-Packard 9000 computer, model 715/60; host station 22 was implemented as model 715/75 of Hewlett-Packard 9000 computer. These computers were interconnected by an I.E.E.E. 802.3 network, and were provided with the HP-UX operating system version 9.03. It should be understood that the invention is not limited by the specific computers, network, and operating system as shown and described herein. Other data processing systems may be used in connection with a database to practice this invention. Such a system may be programmed to embody the present invention, such as by using the HP-C++ programming language and its corresponding compiler. It should be understood that other programming languages and compilers are available for this purpose and the invention is not limited thereby.

In the preferred embodiment of the invention, each data record in the database for a patient includes data elements of which some or all may be associated with a particular a time and date. Such data records may include data elements representative of vital sign information, urine and blood sample analysis results, treatments provided, etc. The database is preferably a relational database, wherein each record is related to a single patient, allowing access to the data by reference to the patient name, among other things. However, the invention is not limited to any particular type of information. The system need only provide sufficient information so that an indication of the current time can be determined and associated with a data element such that the respective patient data represented by the data element may be associated with the current time and recorded as such in the data record. For illustrative purposes, the following description is based on an example of a database having time-stamped data elements representative of patient care events.

Figure 2:
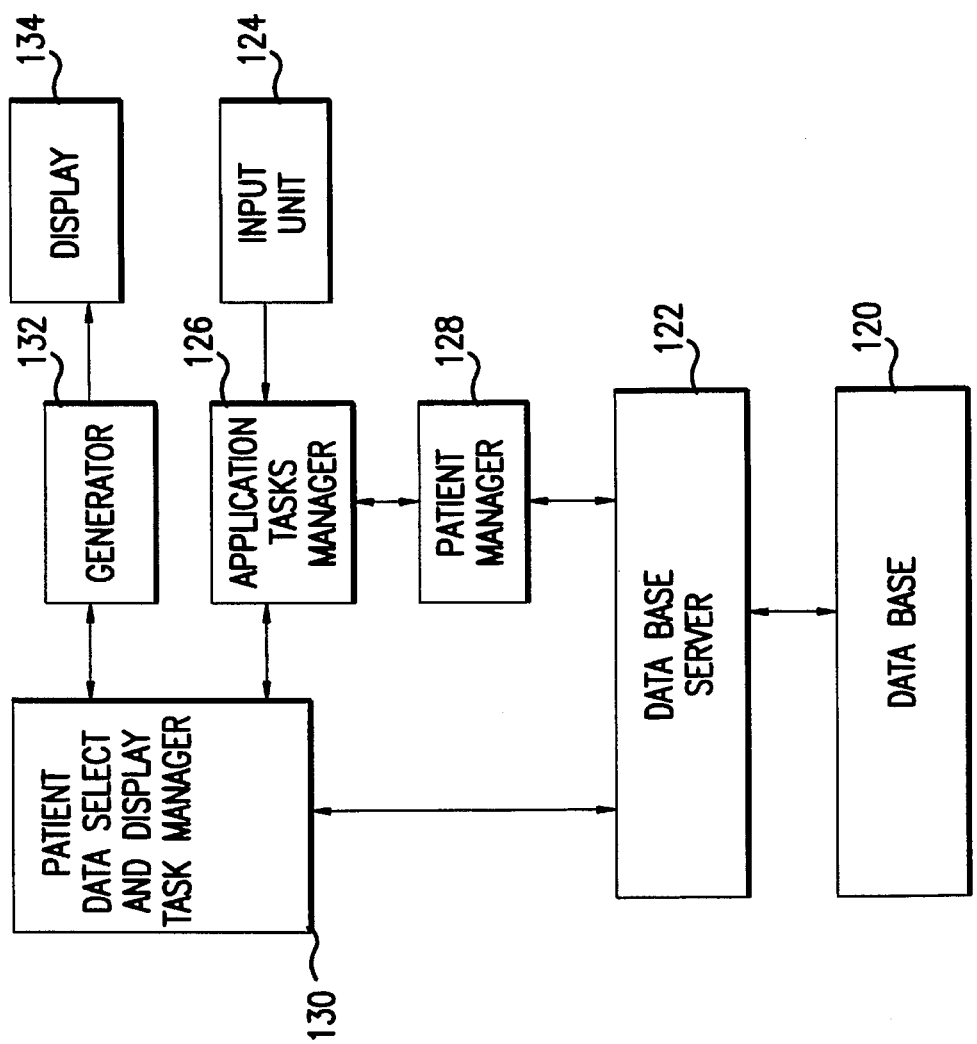
FIG. 2 is a data flow diagram illustrating relationships between modules of a system in accordance with the invention.
Figure 6:
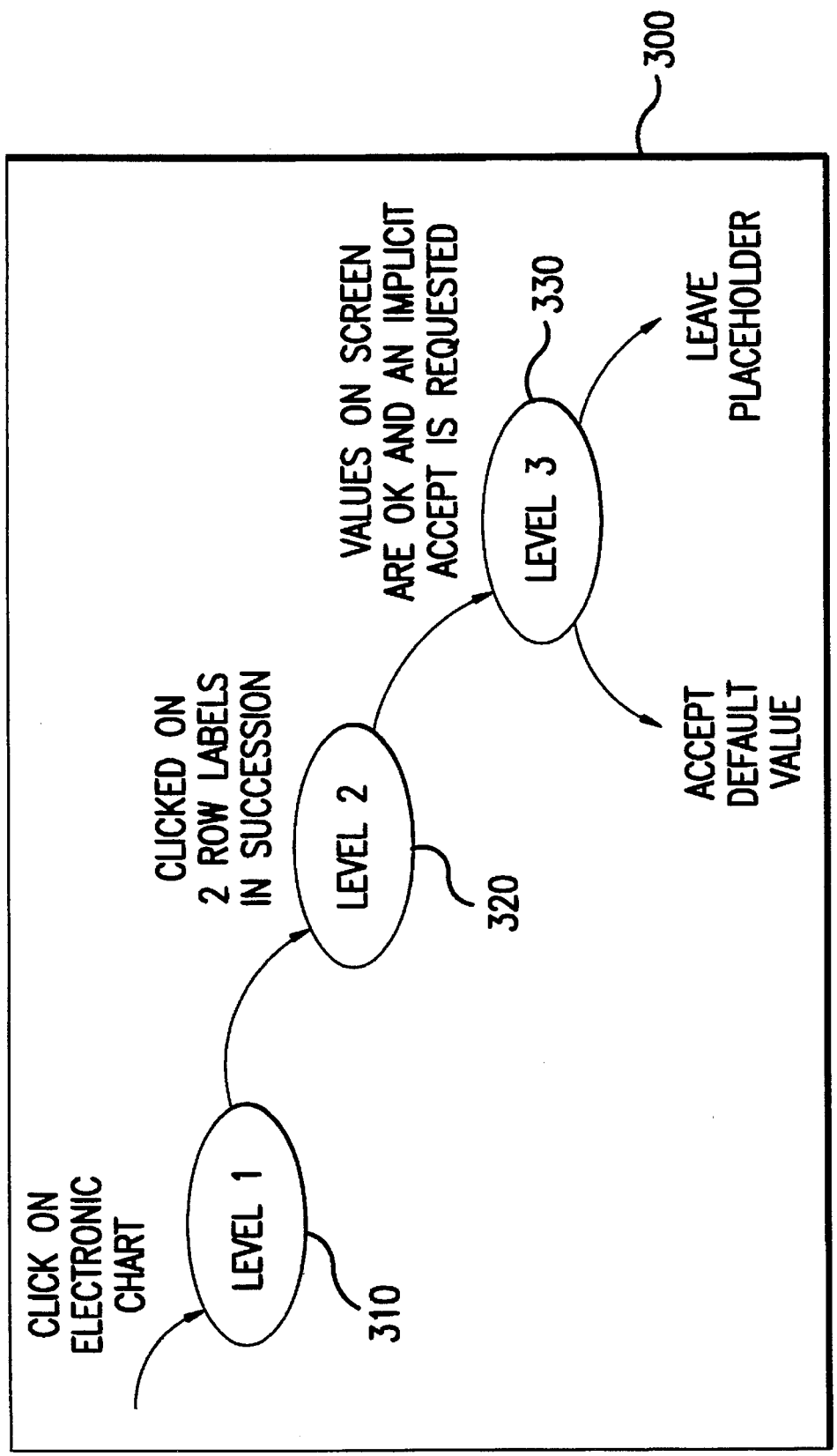
FIG. 6 is a diagrammatic representation of logic filtering steps that are operative in accordance with the present invention.

The preferred embodiment of the invention will now be described in the context of a data flow diagram as represented in FIG. 2. A database 120 stores patient information and is operative in the host station 22 and other host stations in the data processing system 20. Also operative in the host station 22 is a database server 122 which controls access to the database 120. An input unit 124, including the keyboard 42 and/or cursor control device 44, allows a user to provide input signals to an application tasks manager 126 running on a workstation 24, which is an application program suitable for entering and viewing data in the database 120. A patient manager 128 controls the input of patient data to the database 120. If a user indicates, using input unit 124, that viewing of patient data is desired, the application task manager 126 sends such information to the patient data select and display task manager 130. Given the user's input, the patient data select and display task manager 130 determines, using methods described herein, which data record(s) in the patient database 120 to access. The patient data select and display task manager 130 also provides information to a display generator 132 which determines, using methods described below, the information presented on the display 134. The display generator 132 and the patient data select and display task manager 130 provide the appropriate display information to a display 134 which includes the display control 38 and display 40 of the workstation 24 (see also FIG. 1).

Figure 4:
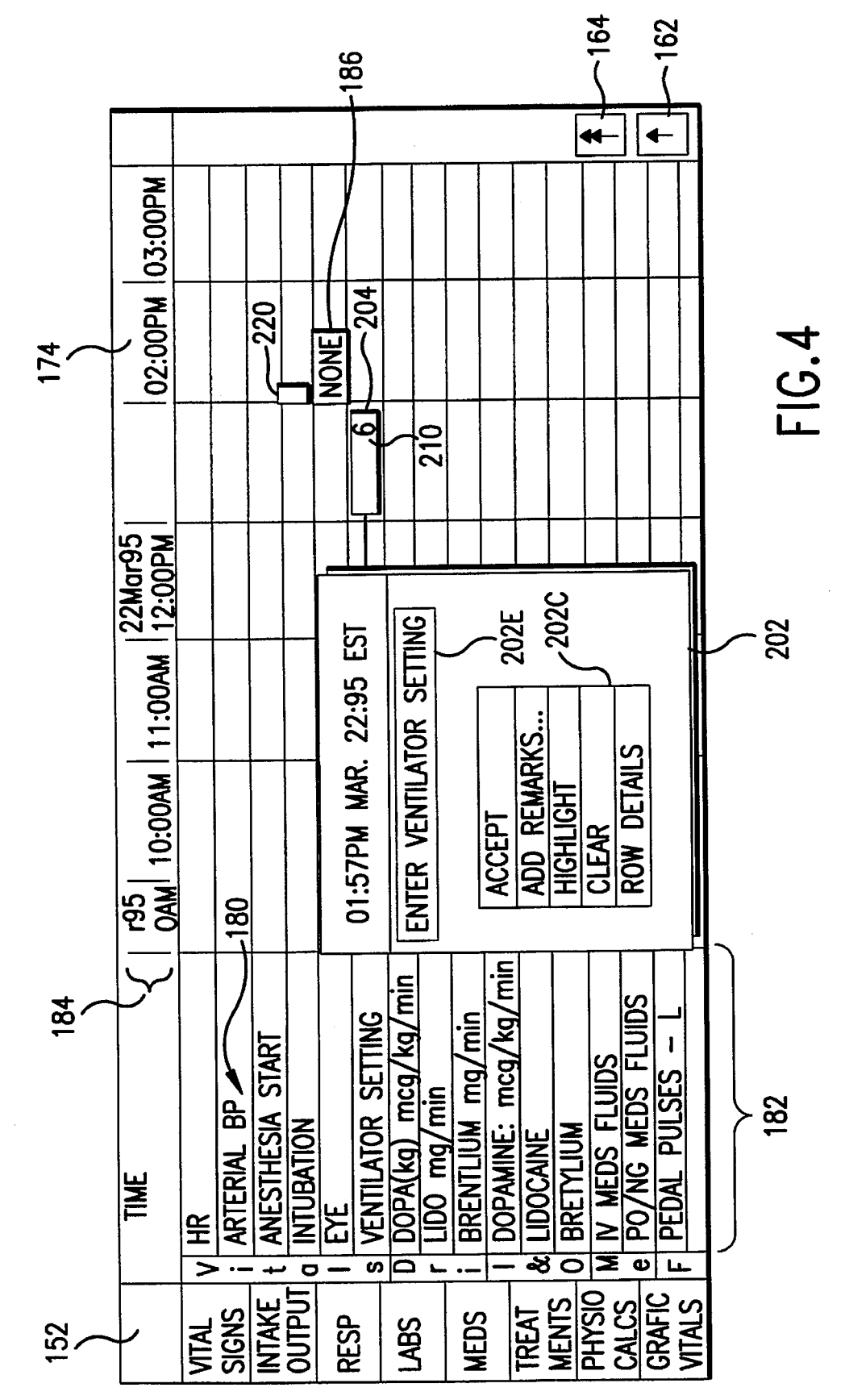

FIGS. 3–5 illustrate suitable graphics for placement on display 40 for use in a computer display system in accordance with the present invention. Similar reference numbers in the figures indicate similar elements. The location of the graphics on the display 40 is not material to this invention; however, it may be preferable to fill the display with the graphics. Such graphics include a data sheet 152 which may be displayed in a manner similar to a conventional flowsheet offered in the HP CareVue 9000 System but in accordance with the present invention as will now be described.

As indicated in FIG. 3, the data are arranged in data sheet 152 chronologically by sample time. The data sheet 152 is made up of a number of columns 170. Each column 170 represents a specific date and time or a period of time (hereinafter, date and time). The date and time represented by each column may be variable and user-selectable. In each column 170, data records are presented in rows 172, wherein each row corresponds to a given type of patient information. Where patient information is found at the intersection of a row and column, the data sheet indicates that the recorded information was obtained at the date and time or during the period of time specified for the indicated column. Each column is preferably labeled with a date label 174 representative of its corresponding date and time.

In the preferred data sheet 152, time is the ordering variable, i.e., the variable used to determine the order in which values of dependent variables are presented. Thus "prior" means earlier and "next" means later. The dependent variables are labeled as row labels 180 in a leftmost row label column 182, whereas time and date labels are indicated in a topmost row 184. Each displayed dependent variable data 186 value is located in a cell at the intersection of the row corresponding to the respective dependent variable and the column representing the time at which the value was measured. The monitor 40 can be expected to permit a plurality of columns and rows of data values to be represented at once; however, differing arrangements of data values are contemplated as well. For example, the flowsheet 152 may include more data than can be conveniently displayed on monitor 40 at any given time. Therefore, data may be scrolled into and out of monitor 40 so that all data can be viewed. A viewing neighborhood of data respectively includes a group of columns within the data sheet 152 for which data can be displayed on monitor 40 at one time.

The preferred embodiment provides a display configuration which is intuitive. Thus, if the information displayed in the data sheet 152 with earliest events at the left and more recent events to the right, for example, the columns should represent the earliest time at the left and current time at the right. Alternatively, the events could be arranged vertically if so desired.

Keys such as arrow key boxes 162, 164 may also be provided in the graphics to facilitate searching for a particular portion of the data sheet 152. Other keys (not shown) may be selected using the cursor control device to access information associated with a time and date that is earlier or later than those already displayed.

With respect to data elements each containing one or more data values represented on the display, a user may enter new data values or modify displayed data values displayed in the data sheet 152 according to one of several data value entry sequences which may be understood as follows.

The user manipulates the input unit 124, e.g., a cursor control device 44 (FIGS. 1–2); in response, the computer positions the cursor 190 on the display 40. When the cursor 190 is located at a point on the display which corresponds to a desired event, the user may generate a signal by suitable operation of the cursor control device. In the preferred embodiment, the user depresses a switch such as is typically found on suitable trackball devices in an action known herein as a "click" to generate a position-dependent signal that is then delivered to the processor 36. In response, the processor 36 then accesses the data record corresponding to the indicated event, date, and time from the data file for the selected patient using well-known data access techniques. The data sheet 152 may then be redisplayed to show data values from the retrieved data record(s). Further manipulation of the cursor control device and the keyboard 42 allow the steps of data value entry and subsequent storage of the modified data record to be performed.

With reference in particular to FIG. 4, when the user provides a first click on a displayed row label, a first data value entry sequence is initiated wherein: a) the row label is highlighted and the event associated with the selected row label is selected; b) a charting dialog 202 is displayed adjacent to the highlighted row label; and c) the current time and the selected event are identified such that a data field 204 is displayed immediately after the first click. The data field 204 is displayed at the intersection of the selected row and the column representative of the current time. While the charting dialog 202 and the data field 204 are displayed, the user may operate the keyboard to enter one or more data values into the data field 204. Keyboard-based data entry affords a simple procedure for entering at least one data value associated with the selected event at the current time. Accordingly, the user can accomplish real time entry of one or more data values associated with the selected event.

According to another feature of the invention, real time data entry is enhanced with the provision of a default data value 210. The data field 204 will at first be displayed as a blank area until a data value is entered by the user. If, however, a default value 210 has been preassigned to the selected event, the default value 210 is considered to be available and is retrieved from memory for display in the data field 204. The default value 210 is then displayed in the data field 204 as a data value to be accepted by the user, or modified by entry of a differing data value. If the default value 210 present in the data field is accepted by the user, the default value 210 is entered in memory as the data value associated with the selected event. The highlighting of the selected row label is then removed, the event associated with the selected row label is no longer selected, and the default value 210 continues to be displayed in the data field.

Whether a data value is entered by the user or provided as a default value, acceptance of the data value present in the data field 204 is performed by the user in one of two ways. In a particular feature of the present invention, the user may simply click again on the selected row label in the data sheet 152 (i.e., perform a second click) to implement an "implicit" acceptance of the displayed data value. Alternatively, the user may operate a designated key in the keyboard 42 to signify an implicit acceptance.

When the user performs a pair of successive clicks wherein the first click is performed on a first row label and the second click is performed on a second, differing row label, (i.e., two successive clicks but on respective first and second row labels 180 in the data sheet 152), the data value entry sequence is modified as follows: a) the row label is highlighted and the event associated with the first highlighted row label is selected; b) a charting dialog 202 is displayed adjacent to the first highlighted row label; c) the current time is identified and associated with the first click; d) the default data value 210 (if any) is displayed in the data field; e) an "implicit accept" of the data visible in the data field 204 is signified by the second click and the default data value is entered for the event associated with the first row label; f) the highlighting of the first row label is removed and the event associated with the first row label is deselected; and g) the second row label is highlighted and its respective event is selected.

The contemplated data entry sequence is especially useful for performing rapid entry of data values when a plurality of events occurs in real time. The user can perform a quick series of click "pairs" to enter a plurality of respective default values.

In another feature of the present invention, the use of a placeholder 220 is contemplated as a means to defer the step of data value entry in the foregoing data entry sequences. Accordingly, in any of the sequences described herein, a data field 204 that is not modified by entry of either a data value (e.g., by use of the keyboard) or by use of a default value is automatically modified to represent a placeholder 220 (preferably represented by an empty box). The placeholder 220 signifies that an action associated with the selected event has been performed at the current time but that the data value associated with the selected event is forthcoming and will be entered at a later time. The contemplated placeholder 220 feature allows the user to record, via a rapid series of click pairs, the occurrences of a group or series of events without the delay incurred by entry of data values at each event. Each placeholder 220 thereby occupies (temporarily) the intersection of the selected row and the current time column much like a displayed dependent variable data value 186. Thus, when the data value for a particular placeholder 220 is subsequently entered, that data value will be associated with the exact time of the creation of the placeholder 220 which then becomes a dependent variable data value 186.

Each placeholder 220 will be preserved on the data sheet 152 as a temporary field for the duration of a mode of operation considered herein as a charting mode; however, within the charting mode, each placeholder 220 remains only until the user returns the cursor to the placeholder 220 and enters the necessary data value. Once a placeholder 220 is accessed, it is assumed the user wishes to complete the steps of data entry for the selected event. Access of a placeholder 220 is initiated by locating the cursor 190 on the placeholder 220 and clicking once. The placeholder 220 is immediately removed and the user is again presented with a charting dialog 202 to allow entry of a data value to be associated with the selected event at the time of the former placeholder 220. The user, while presented with the charting dialog 202, has the choice of clearing (i.e., deleting) the placeholder 220 or editing (i.e., entering) a data value. In the preferred embodiment, the charting dialog 202 accepts only a clear function 202C or edit function 202E and therefore the user has but one opportunity to act on the placeholder 220. In other embodiments, additional opportunities can be provided if necessary.

All placeholders 220 not acted upon are removed from the data sheet 152 upon exiting charting mode. Alternatively, it is contemplated that a valid data entry interval may be predefined to start upon the creation of each placeholder 220. Upon the expiration of each valid data entry interval, the respective placeholder 220 would be cleared automatically.

Additional features of the invention are contemplated to assist the user in performing data entry. It is contemplated that in response to operation of the cursor control device 44 and activation of switches, the computer may also perform a number of functions to facilitate selection of a desired date and time. For example, when the cursor is moved into the data field 204, as may be detected using conventional techniques, the border of the data field 204 may be thickened to indicate that the data field 204 is activated. When the cursor is moved out of the box data field 204, its border returns to its normal width and no data may be applied to the data field 204. In another preferred embodiment, the cursor 190 may also be made to disappear and a vertical bar to appear when the cursor 190 enters the data field 204.

With reference now to FIG. 7, a series of filter logic levels 300 may be understood to implement some of the processing tasks described above with reference to implicit acceptance and the creation of a placeholder 220. In the preferred implementation of the filter logic, there is a determination of a selected row (type of event) and column (time); a differentiation between a request to chart new values, a request to view old value, and a request to perform implicit accept operations; and if an implicit accept is desired, a determination of whether to accept a default value or to create a placeholder 220. The preferred implementation is accomplished via three levels 310, 320, 330 of filtering logic.

When a user clicks a location on the data sheet 152, the following logic, expressed herein in pseudocode, is implemented:

```
Level 1 filtering logic:
if (previous click was on a row label)
AND
(current click is also on a row label)
then
   goto Level 2 filtering logic
Level 2 filtering logic:
make sure any value for the current charting dialog is
   valid
if it is not,
   display an error message
   end filtering (no implicit accept can occur)
otherwise, continue filtering
if (current crick occurred in same section as previous
   click)
   goto Level 3 filtering logic
Level 3 filtering logic:
if (there is a default for this event at this time)
   accept the default value and put in on the flowsheet
otherwise
if (there is no value charted at this time yet)
   leave a placeholder 220
```

What is claimed is:

1. A method for facilitating entry of patient information in a medical information system, the medical information system including a computer with an input unit, a display and a database containing a data record, the method comprising the steps of:

displaying at least a portion of said data record in the form of an electronic data sheet having plural data elements each representative of patient care information associated with a time and date;

receiving a first input from the input unit, said first input including event information representative of a selected event;

receiving a second input from the input unit, said second input including a data value representative of a data value to be associated with the selected event;

in response to one of said first and second inputs, determining current time information to be associated with the data value;

in response to said second input, causing said current time information, data value, and selected event to be associated to provide an associated data value; and entering said associated data value as said data element in said data record.

2. The method of claim 1, wherein the selected event represents a patient care event.

3. The method of claim 2, further comprising the step of displaying the associated data value as said data element in said display.

4. The method of claim 3, wherein said display step provides said electronic flowsheet in a tabular format, and further comprising the step of displaying the associated data value as said data element in a portion of said electronic flowsheet, and said electronic flowsheet portion being representative of the current time information.

5. The method of claim 4, wherein said electronic flowsheet portion is represented as a column in said electronic flowsheet, and said event is represented as a row in said electronic flowsheet.

6. The method of claim 1, wherein the input unit is a keyboard, and the data value associated with the patient care event is provided by manipulation of the keyboard.

7. The method of claim 1, wherein the input unit is a cursor pointing device, and at least one of the step of receiving said first input and the step of receiving said second input is provided by manipulation of the cursor pointing device.

8. The method of claim 1, wherein the input unit is a cursor pointing device, and in at least one of the step of receiving said first input and the step of receiving said second input, the value associated with the patient care event is provided by manipulation of the cursor pointing device.

9. The method of claim 1, further comprising the step of providing a default data value for acceptance as the data value, and wherein said second input signifies implicit acceptance of the default value.

10. The method of claim 9, wherein the step of providing a default data value for acceptance as the data value is provided upon the occurrence of said first input.

11. The method of claim 1, further comprising the step of retrieving and displaying a data value stored in said data record for acceptance as the data value, and wherein said second input signifies implicit acceptance of the default value.

12. The method of claim 11, wherein the step of providing a data value already present in said data record for acceptance as the data value is provided upon the occurrence of said first input.

13. The method of claim 1, further comprising the step of providing a placeholder for acceptance as the data value, and wherein said second input signifies implicit acceptance of the default value.

14. The method of claim 13, wherein the step of providing a placeholder for acceptance as the data value is provided upon the occurrence of said first input.

* * * * *